United States Patent [19]

Ushikubo

[11] Patent Number: 4,710,355
[45] Date of Patent: Dec. 1, 1987

[54] REAGENT DELIVERY DEVICE

[75] Inventor: Masao Ushikubo, Hachioji, Japan

[73] Assignee: Olympus Optical Co., Ltd., Tokyo, Japan

[21] Appl. No.: 743,389

[22] Filed: Jun. 11, 1985

[30] Foreign Application Priority Data

Jun. 14, 1984 [JP] Japan ................................ 59-120640
Aug. 18, 1984 [JP] Japan ................................ 59-171001

[51] Int. Cl.⁴ .......................... B01L 3/02; G01N 37/00
[52] U.S. Cl. .................................... 422/100; 222/135; 222/144.5; 422/63; 422/81; 422/103
[58] Field of Search ................... 422/63, 64, 65, 67, 422/73, 81, 100, 103; 222/135, 144.5

[56] References Cited

U.S. PATENT DOCUMENTS

| 3,881,872 | 5/1975 | Naono | 422/81 |
| 4,207,074 | 6/1980 | Suzuki | 422/63 |
| 4,244,919 | 1/1981 | Chen | 422/63 |
| 4,325,907 | 4/1982 | Dembicki, Jr. et al. | 422/80 |
| 4,351,799 | 9/1982 | Gross et al. | 422/63 |

FOREIGN PATENT DOCUMENTS

| 58-87462 | 5/1983 | Japan | 422/64 |
| 58-76764 | 5/1983 | Japan | |
| 59-32868 | 2/1984 | Japan | 422/64 |

Primary Examiner—Michael S. Marcus
Attorney, Agent, or Firm—Parkhurst & Oliff

[57] ABSTRACT

A reagent delivery device includes a plurality of delivery syringes, and a plurality of units each having rotary valves by which respective reagent tanks and delivery nozzles are selectively connected with each other and a driving means for driving the rotary valves simultaneously. Further, in the reagent delivery device, the delivery syringes are respectively connected to the rotary valves through the manifold blocks, and a washing liquid is flows through the syringes and manifold blocks. Therefore, if it is necessary to increase the number of reagents to be delivered, such a requirement can be easily dealt with by arranging additional units and manifold blocks without increasing the number of delivery syringes, and contamination between reagents can be eliminated.

7 Claims, 42 Drawing Figures

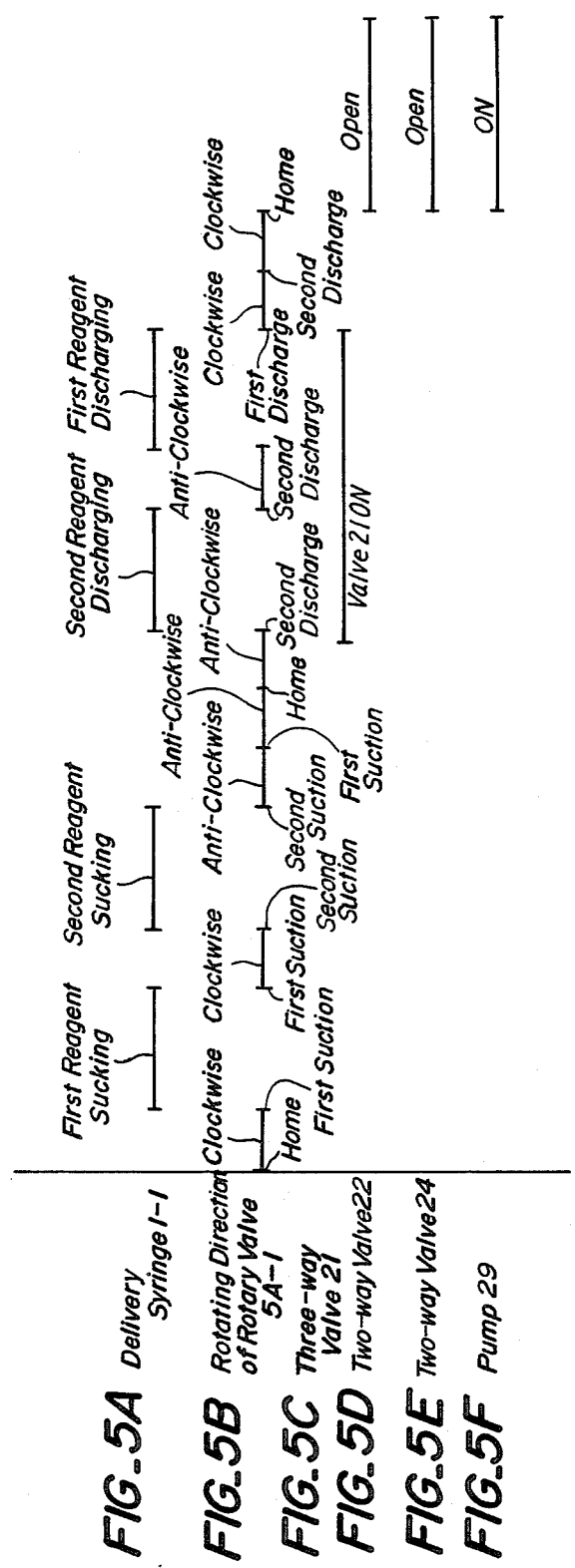

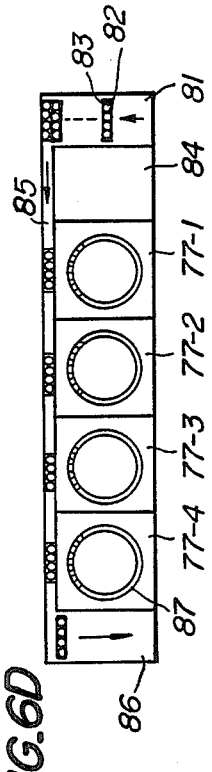
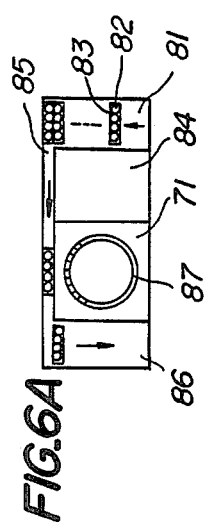
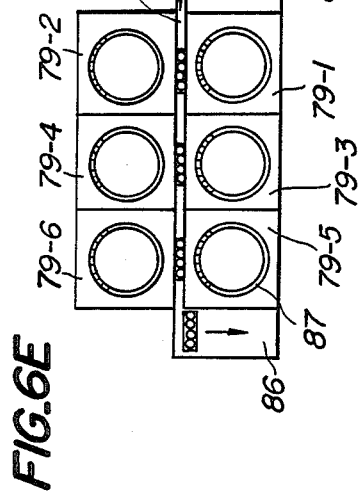
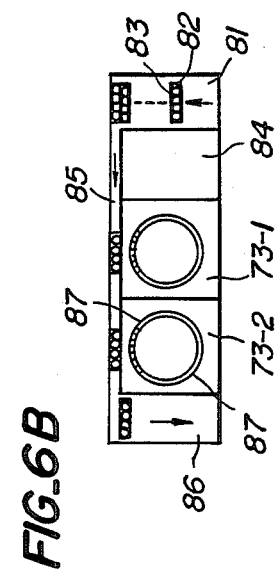
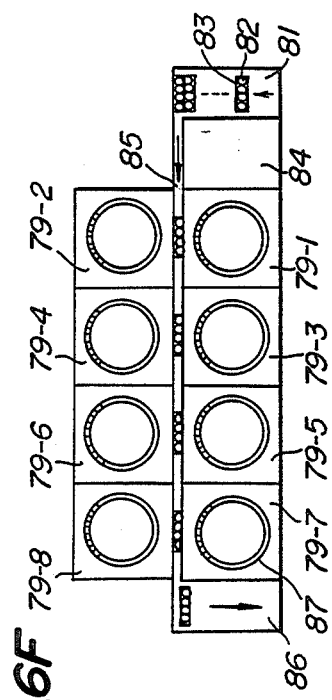
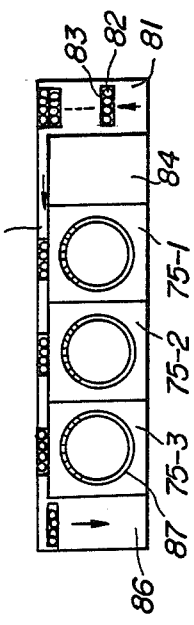

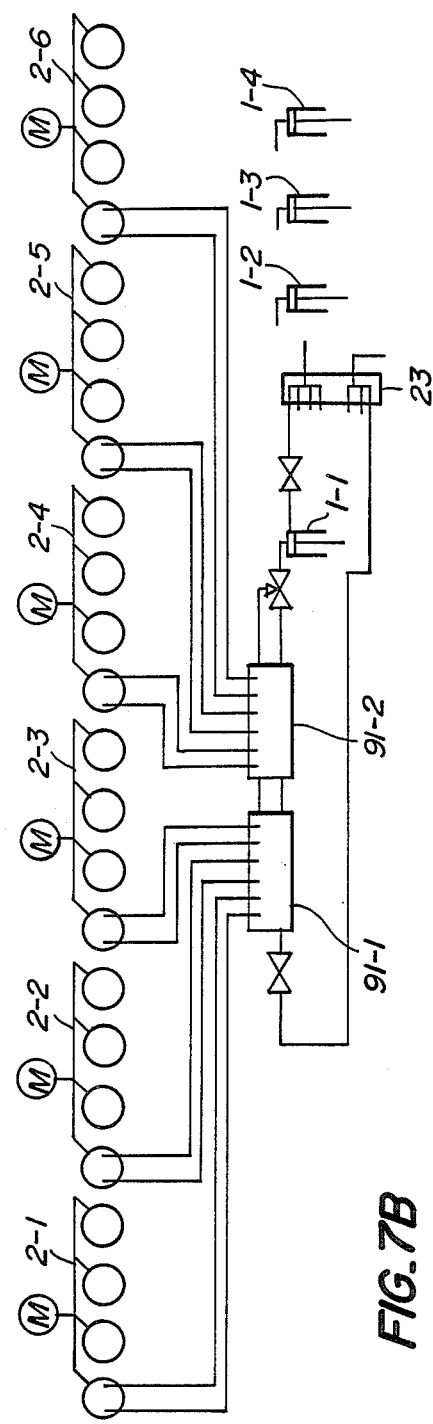
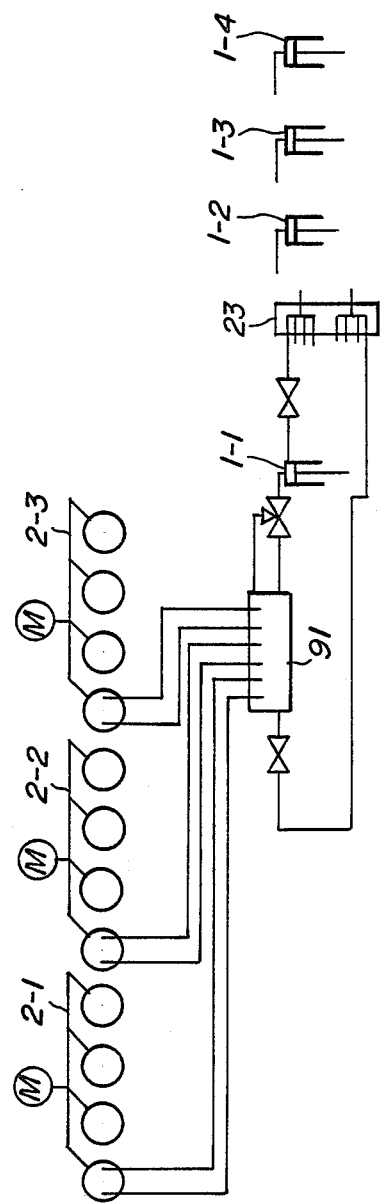
FIG. 7A
FIG. 7B

FIG_10A
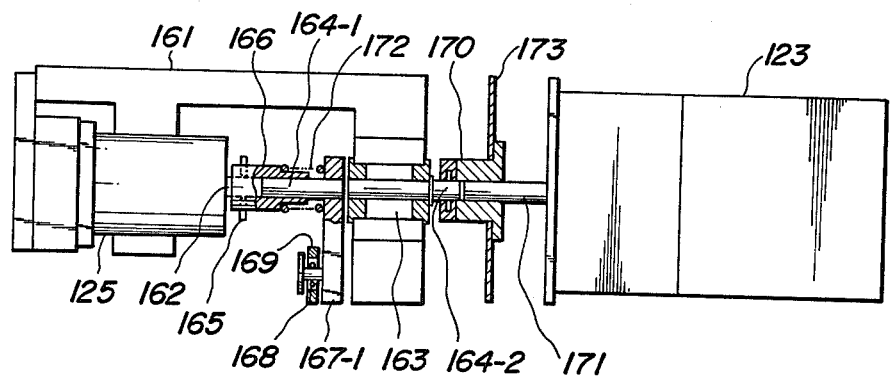
FIG_10B
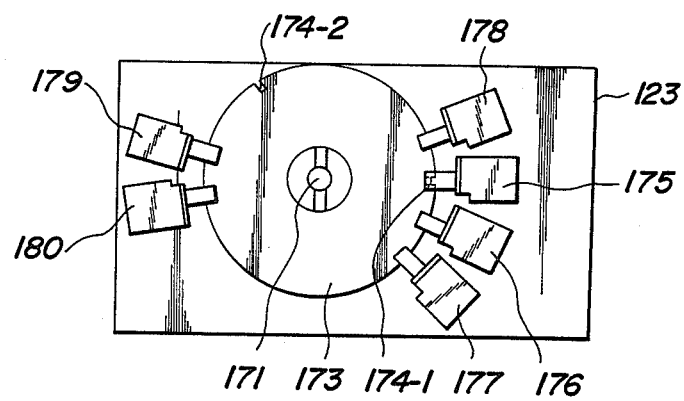
FIG_10C
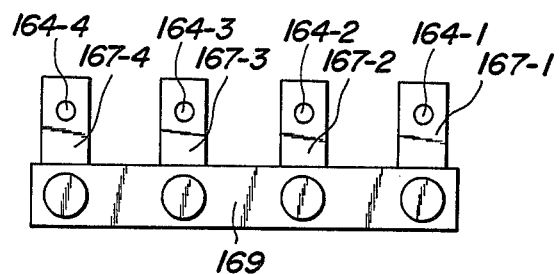

FIG_11A
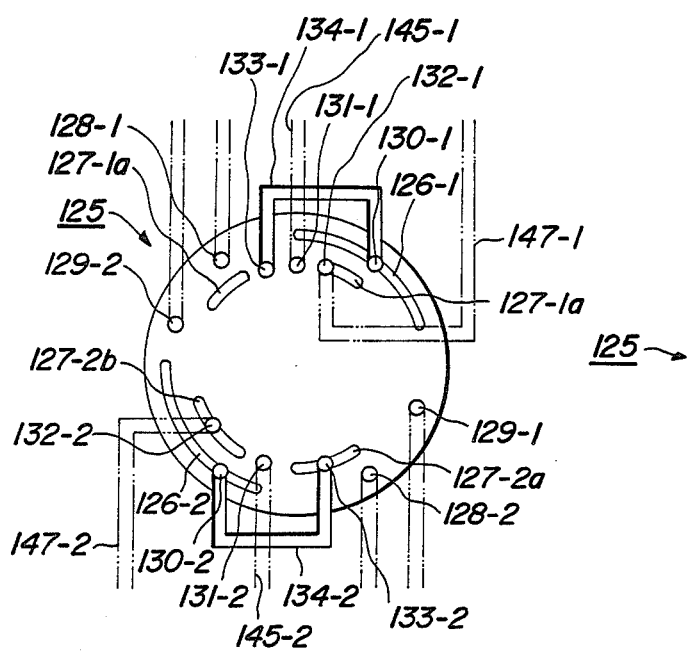
FIG_11B
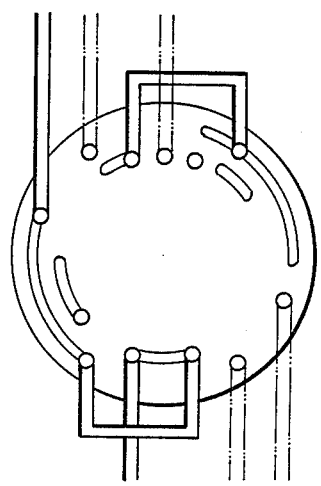
FIG_11C
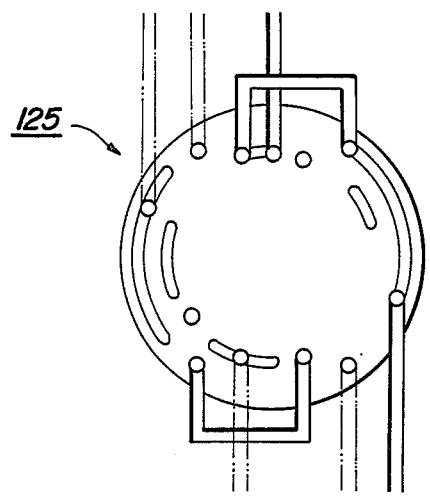

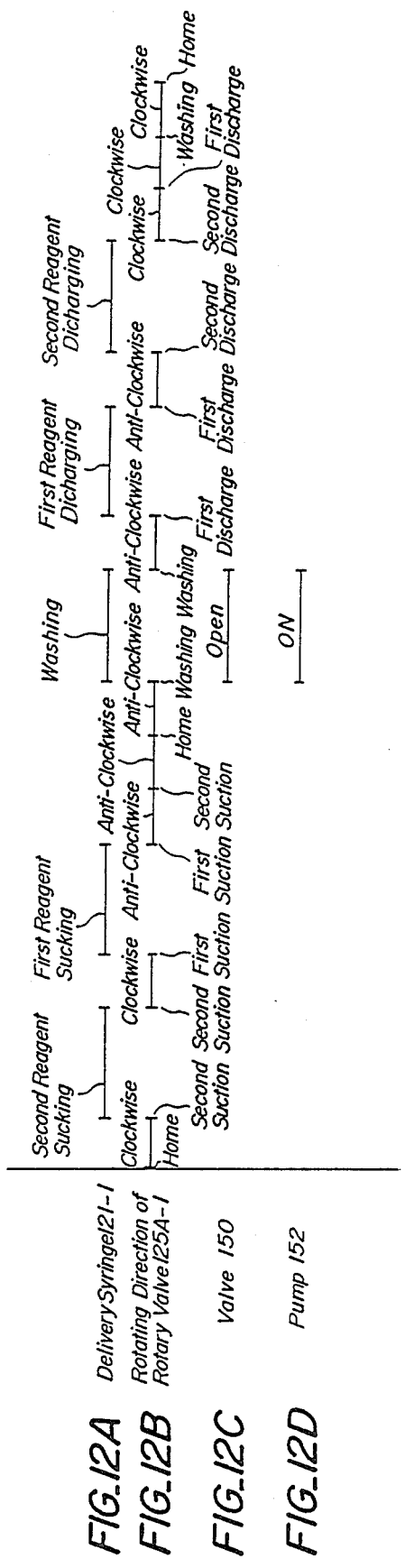

REAGENT DELIVERY DEVICE

BACKGROUND OF THE INVENTION

1. Field of the Invention:

The present invention relates to a reagent delivery device which is preferably used for an automatic chemical analyzer.

2. Description of the Background Art:

In an automatic chemical analyzer, use is made of various kinds of reagents for effecting multi-item analysis. In a known reagent delivery device for delivering plural kinds of reagents, there has been proposed (1) a device having plural pairs of delivery syringes and a delivery nozzle corresponding to respective reagents, (2) a device having one common pair of delivery syringes and a delivery nozzle, which function to selectively deliver a number of reagents by moving the delivery nozzle and (3) a device having a rotary flow-line changing valve which functions to change a plurality of reagent flow-lines one by one, as disclosed in Japanese Patent Laid-open Publication No. 76,764/83.

However, in delivery device (1), since it is necessary to provide a number of delivery syringes corresponding to the number of the reagents, the chemical analyzer including delivery device (1) is liable to be large in size. Moreover, delivery device (2) having one common pair of delivery syringe and nozzle has a drawback in that a syringe moving mechanism is complicated and contamination between reagents is liable to occur. Further, in delivery device (3) using the rotary flow-line changing valve, when the reagent is diluted by a washing liquid serving also as a diluting liquid, the flow-line changing valve can be effectively used without causing contamination between reagents, since the reagent is flows away from the valve by the washing liquid. However, when only reagent is delivered, there a drawback occurs in that reagent delivery becomes impossible, because contamination between reagents is caused due to the washing liquids remaining in the flow-lines from the valve to respective reagent discharging outlets.

Furthermore, in an automatic chemical analyzer, sometimes it is necessary to increase the number of channels i.e. the number of test items. However, in delivery device (1), it is necessary to arrange additional delivery syringes in response to the increase of the reagents, and thus the operation for this additional arrangement becomes extremely troublesome and the chemical analyzer including such a delivery device becomes complicated in construction. Moreover, in delivery device (2), if the reagents are concentrically set in a turntable and the reagent is sucked by the delivery nozzle at a predetermined position, it is easy to deal with the increase of the delivery reagents. However, in this case, there remains a problem of contamination between reagents. Further, in the delivery device (3), if the flow-line changing valve is exchanged, it is easy to accomodate the increase of reagents, but the valve exchanging operation is extremely troublesome and a chemical analyzer including such a delivery device becomes complicated in construction.

SUMMARY OF THE INVENTION

The present invention has for its object to eliminate the drawbacks mentioned above, and to provide a reagent delivery device which can selectively deliver a plurality of reagents without causing contamination therebetween and which can easily deal with an increase of reagents to be delivered.

According to the invention, a reagent delivery device comprises, a plurality of sucking and discharging means;

a plurality of units connected to said sucking and discharging means, each having valves the number of which corresponds to the number of sucking and discharging means, and a driving means for simultaneously driving the valves;

a plurality of reagent tanks connected to the valves in which plural kinds of reagents are respectively contained;

a plurality of delivery nozzles connected to the valves; and a plurality of manifold block means each being connected to respective sucking and discharging means having a plurality of flow-lines each of which is connected to one of the valves in respective units; whereby respective delivery nozzles and reagent tanks are selectively connected to said sucking and discharging means by an operation of said valves.

BRIEF DESCRIPTION OF THE DRAWINGS

FIGS. 4A to 4E and FIGS. 5A to 5F are schematic views for explaining the operation of the rotary valve according to the invention;

FIGS. 6A to 6F are schematic views showing one embodiment of an automatic chemical analyzer having the reagent delivery device according to the invention;

FIGS. 7A to 7D are schematic views illustrating a main portion of the reagent delivery device shown in FIGS. 6A to 6F;

FIGS. 10A to 10C are schematic views illustrating one embodiment of a unit shown in FIG. 8; and FIGS. 11A to 11F and FIGS. 12A to 12D are schematic views for explaining the operation of the rotary valve used in the embodiment shown in FIG. 8.

DESCRIPTION OF THE PREFERRED EMBODIMENTS

Figure 1:
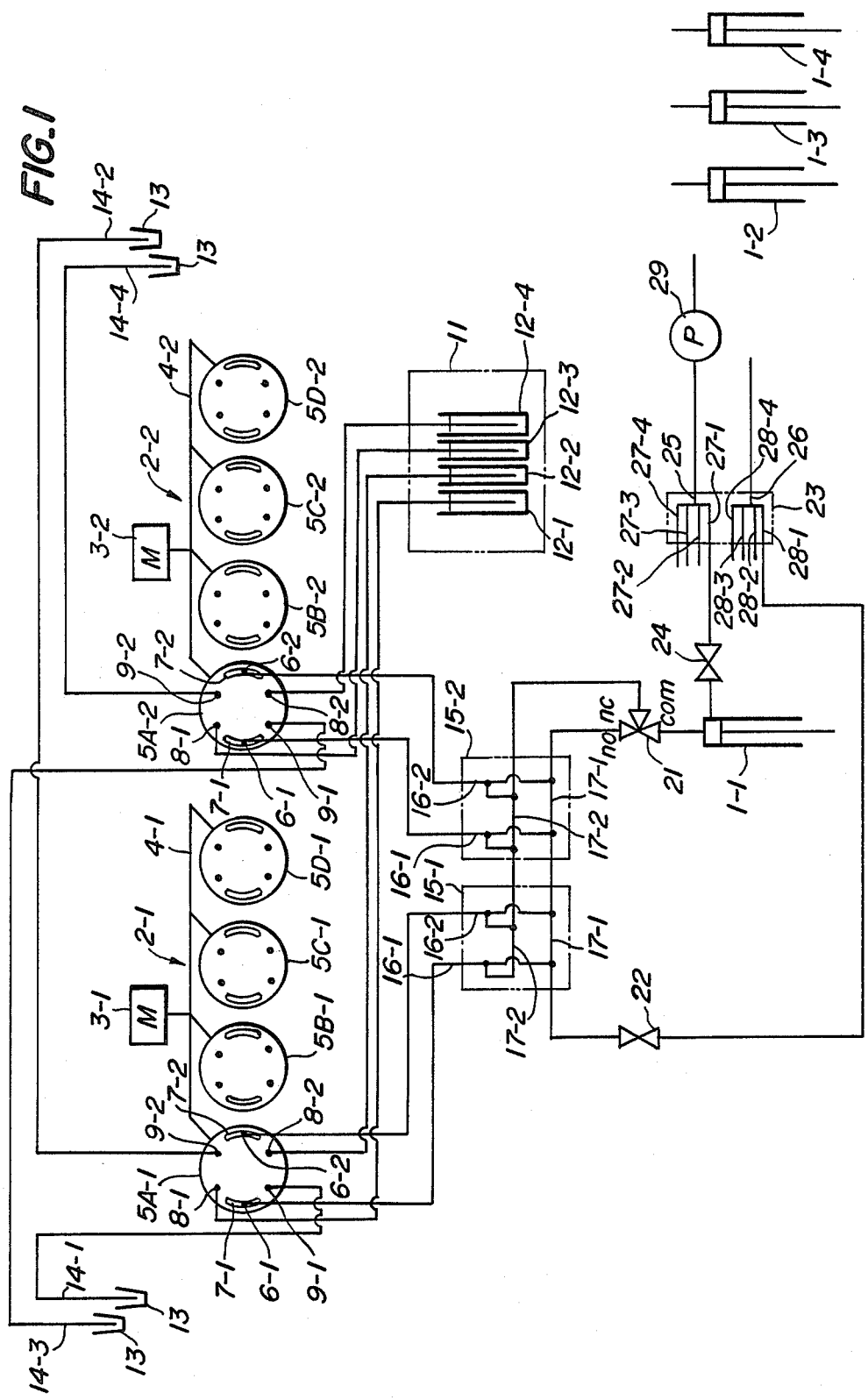
FIG. 1 is a schematic view showing one embodiment of the reagent delivery device according to the invention.

FIG. 1 is a schematic view showing one embodiment of the reagent delivery device according to the invention. In this embodiment, use is made of four delivery syringes 1-1 to 1-4 and two units 2-1 and 2-2. The units 2-1 and 2-2 having the same construction comprise respectively motors 3-1 and 3-2 driven independently from each other and four rotary valves 5A-1 to 5D-1 and 5A-2 to 5D-2 which are simultaneously driven by the motors 3-1 and 3-2 via driving mechanisms 4-1 and 4-2. Each rotary valve corresponds to one channel i.e. one test item, and functions to deliver selectively a first reagent and a second reagent of different kinds. To this end, each rotary valve comprises first and second common holes 6-1, 6-2 corresponding to the first and second reagents, and first and second suction holes 8-1, 8-2 and first and second discharge holes 9-1, 9-2 which are connectable selectively to first and second common holes 6-1, 6-2 through first and second long recesses 7-1, 7-2.

In the unit 2-1, the first and the second suction holes 8-1 and 8-2 of one rotary valve 5A-1 are respectively connected to first and second reagent tanks 12-1 and 12-2 contained in a reagent refrigerator 11. First and second discharge holes 9-1 and 9-2 are connected respectively to delivery nozzles 14-1 and 14-2 arranged at predetermined positions through which a reaction vessel 13 containing a sample liquid to be tested is transported along a first reaction line. Moreover, first and second common holes 6-1 and 6-2 are respectively connected to a manifold block 15-1 having two flow-lines. The manifold block 15-1 comprises two flow-lines 16-1 and 16-2, and first and second common flow-lines 17-1 and 17-2 connected respectively to the flow-lines 16-1 and 16-2. The flow-lines 16-1 and 16-2 are respectively connected to the first and second common holes 6-1 and 6-2 of the rotary valve 5A-1.

Also in the unit 2-2, first and second suction holes 8-1, 8-2 of the rotary valve 5A-2 are respectively connected to first and second reagent tanks 12-3, 12-4 contained in the reagent refrigerator 11. First and second discharge holes 9-1, 9-2 are respectively connected to delivery nozzles 14-3, 14-4 arranged at predetermined positions through which a reaction vessel 13 containing a sample liquid is transported along a second reaction line. Moreover, first and second common holes 6-1, 6-2 are respectively connected to the flow-lines 16-1, 16-2 in manifold block 15-2 having the same construction as that of the manifold block 15-1.

In the manifold blocks 15-1 and 15-2 to which the rotary valves 5A-1 and 5A-2 are respectively connected, first flow-lines 17-1 and 17-1 and second flow-lines 17-2 and 17-2 are respectively connected with each other. One end of the first common flow-line is connected to a normally open port (no) of a three-way valve 21, and the other end thereof is connected to as branch block 23 through a two-way valve 22. The second common flow-line is connected to a normally closed port (nc) of the three-way valve 21. Moreover, a common port (com) of the three-way valve 21 is connected to the branch block 23 through the delivery syringe 1-1 and a two-way valve 24. The branch block 23 comprises two main flow-lines 25 and 26, and four branch flow-lines 27-1 to 27-4 and 28-1 to 28-4 connected respectively to the main flow-lines 25 and 26. One branch flow-line 27-1 connected to the main flow-line 25 is connected to the two-way valve 24, and one branch flow-line 28-1, connected with the main flow-line 26, is connected to the two-way valve 22. Moreover, the main flow-line 25 is connected to a washing liquid tank not shown through a pump 29, and the main flow-line 26 is connected to a waste liquid tank now shown.

Heretofore, the explanation was made with respect to one delivery syringe 1-1, but the other delivery syringes 1-2 to 1-4 have the same construction as that of the delivery syring 1-1. For example, the rotary valves 5B-1, 5B-2; 5C-1, 5C-2; 5D-1, 5D-2 can be respectively connected to the syringes 1-2; 1-3; 1-4 by means of respective two manifold blocks and a three-way valve. The delivery syringes 1-2 to 1-4 can be respectively connected to the branch flow-lines 27-2 to 27-4 of the branch block 23 through a two-way valve, and the first common flow-lines of the respective two manifold blocks connected therebetween can be connected to the branch flow-lines 28-2 to 28-4 through the two-way valve.

In this embodiment, a maximum of sixteen kinds of reagents can be selectively delivered by means of the syringes 1-1 to 1-4, but if it is necessary to use further reagents, additional units may be provided and may be respectively connected to the delivery syringes 1-1 to 1-4 in the same manner mentioned above through additional manifold blocks or through manifold blocks each having additional flow-lines.

Figure 2A:
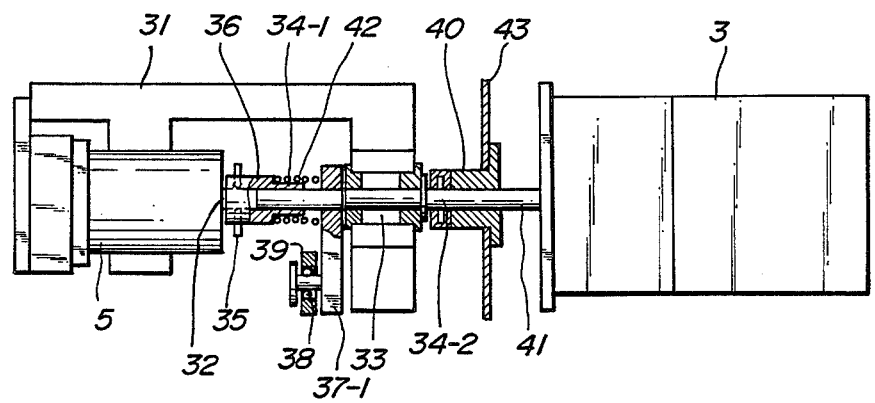
FIGS. 2A to 2C are schematic views illustrating one embodiment of a unit shown in FIG. 1.
Figure 2B:
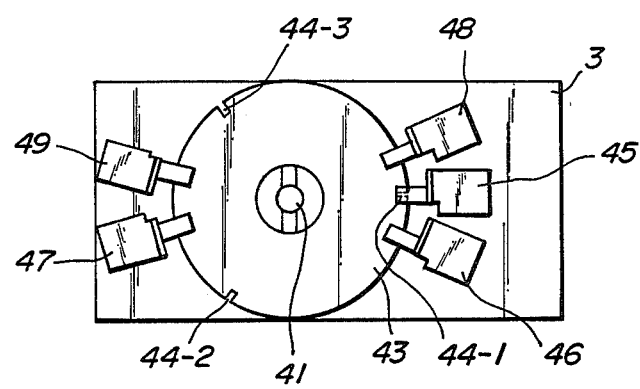
Figure 2C:
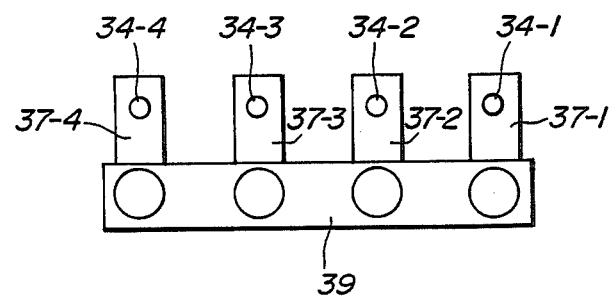

FIGS. 2A to 2C are schematic views showing one embodiment of the unit according to the invention. In this embodiment, use is made of four rotary valves, but only one rotary valve 5 is shown for the sake of simplicity. These four rotary valves are supported by a base 31, and respective drive shafts 32 of these rotary valves are respectively connected through drive pins 35 to one end of valve drive shafts 34-1 to 34-4 rotatably secured to the base 31 via bearings 33. Respective drive pins 35 are supported by respective pin holders 36. Valve driving shafts 34-1 to 34-4 are secured to one end of respective levers 37-1 to 37-4, the other ends of which are connected to a connection plate 39 through bearings 38. In addition, the other end of one valve drive shaft (in the FIGS. 2A to 2C the valve drive shaft 34-2) is connected to an output shaft 41 of the motor 3 through a coupling 40. In this manner, four valve drive shafts 34-1 to 34-4, i.e. respective drive shafts 32, are simultaneously driven through the levers 37-1 to 37-4 and the connection plate 39 by means of one motor 3. Further, coil springs 42 are respectively arranged between the levers 37-1 to 37-4 and the pin holders 36.

The four rotary valves 5 are constructed to be simultaneously driven between a home state, a first reagent sucking state, a second reagent sucking state, a second reagent discharging state and a first reagent discharging state. In order to detect the respective states mentioned above, a detection plate 43 is secured to the coupling 40 and three cut-out portions 44-1 to 44-3 are formed at predetermined positions in the detection plate 43. Then, the positions of the cut-out portions 44-1 to 44-3 each representing the current states can be detected by means of a home sensor 45, a first suction sensor 46, a second suction sensor 47, a second discharge sensor 48 and a first discharge sensor 49 each consisting of a photo-interrupter, which are arranged fixedly on the base 31 at predetermined positions.

Figure 3A:
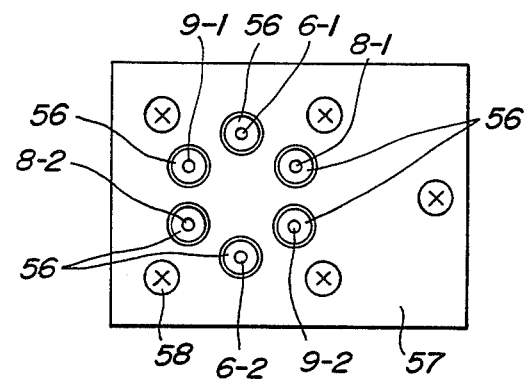
FIGS. 3A and 3B are a plan and a cross sectional views, respectively, depicting one embodiment of a rotary valve shown in FIG. 1.
Figure 3B:
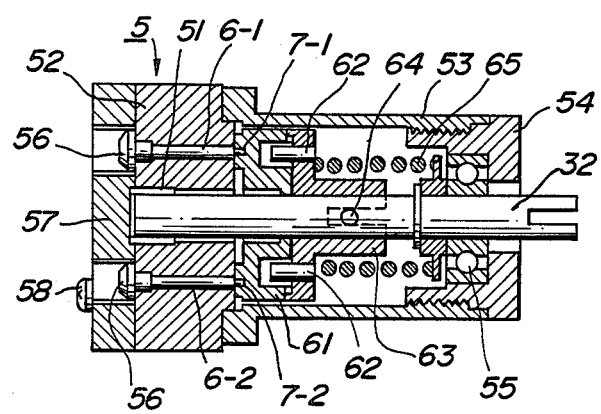

FIGS. 3A and 3B show one embodiment of the rotary valve 5. One end of the drive shaft 32 is secured to a valve head 52 through a bearing 51, and the other end thereof is secured to a housing 54 fixed to an end portion of a cylindrical housing 53 through a bearing 55. First and second common holes 6-1 and 6-2, first and second suction holes 8-1 and 8-2, and first and second discharge holes 9-1 and 9-2 are formed in the valve head 52 concentrically with respect to the drive shaft 32. Moreover, as shown in FIG. 3B, metal caps 56 are arranged at one end of respective holes, and a valve support plate 57 is connected to the valve head 52. The valve support plate 57 and the valve head 52 are secured to the housing 53 by means of screws 58.

To the other end of the valve head 52 is coaxially arranged a change-over valve 62 having circular arc shaped first and second long recesses 7-1 and 7-2. These first and second long recesses having a circular arc shape function to connect selectively first and second common holes 6-1, 6-2 with first and second suction holes 8-1, 8-2 and first and second discharge holes 9-1, 9-2. A valve support 63 is arranged coaxially with respect to the drive shaft 32 by engaging a pin 62 of the valve support 63 with the change-over valve 61. Further, a pin 64 pierced into the drive shaft 32 in a radial direction is engaged with the valve support 63, whereby the valve support 63 and thus the change-over valve 61 are integrally rotated with the drive shaft 32. In addition, the valve support 63 is urged against the valve head 52 by means of a coil spring 65 so as to keep a liquid tight friction plane between the valve head 52 and the change-over valve 61.

Hereinafter, the operation of this embodiment will be explained with reference to FIGS. 1, 4A to 4E and FIGS. 5A to 5F.

(1) Initialization of delivery device:

In this explanation, the operation of one rotary valve 5A-1 of the unit 2-1 will be explained, since the operations of the other rotary valves 5B-1 to 5D-1 and 5A-2 to 5D-2 are entirely the same as that of the valve 5A-1. At the home state in which the home sensor 45 detects the cut-out portion 44-1 formed in the detection plate 43 (see FIG. 2B), the rotary valves of respective units 2-1 and 2-2 maintain such a condition that first and second long recesses 7-1 and 7-2 are respectively connected only to first and second common holes 6-1 and 6-2 as shown in FIG. 4A.

Then, by driving the motor 3-1 of the unit 2-1, the detection plate 43 is rotated in an anti-clockwise direction until the first discharge sensor 49 detects the cut-out portion 44-3 in FIG. 2B. At this position, the home state has been changed into the first reagent discharging state such that only the first common hole 6-1 and the first discharging hole 9-1 are connected with each other through the first long recess 7-1 as shown in FIG. 4E. In this state, the pump 29 is actuated under the condition that a com-no pass is opened by turning the three-way valve 21 OFF, the two-way valve 24 is opened and the two-way valve 22 is closed, and the washing liquid is discharge from the delivery nozzle 14-1 through the com-no passage of the three-way valve 21, the first common flow-line 17-1 of the manifold blocks 15-2, 15-1 and the rotary valve 5A-1.

Figure 4A:
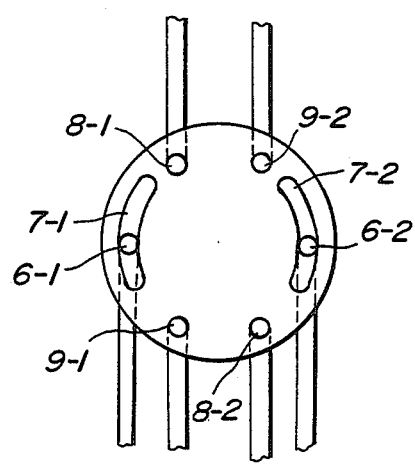

Then, the state of the rotary valve 5A-1 is changed into the home state shown in FIG. 4A, and the pump 29 is actuated again under this condition except that the two-way valves 22 and 214 are opened. Under such a condition, washing liquid is discharged from the main flow-line 26 through the com-no passage of the three-way valve 21, the first common flow-lines 17-1 of the manifold blocks 15-2 and 15-1, the two-way valve 22 and the branch block 23, and thus all the flow-lines are filled with washing liquid.

Then, the state of the rotary valve 5A-1 is changed into the first reagent discharge state shown in FIG. 4E, and the pump 29 is actuated again under the condition that a com-no passage is opened by turning the three-way valve 21 ON, the two-way valve 24 is opened and the two-way valve 22 is closed, so that the washing liquid is discharged from the delivery nozzle 14-1 through the com-nc passage of the three-way valve 21, the second common flow-lines 17-2 of the manifold blocks 15-2, 15-1, and the rotary valve 5A-1.

By effecting the above operations, the flow-line from the delivery nozzle 14-1 to the first discharge hole 9-1 of the rotary valve 5A-1, and all the flow-lines connected to the first long recess 7-1 and the first common hole 6-1 are filled with the washing liquid.

Figure 4B:
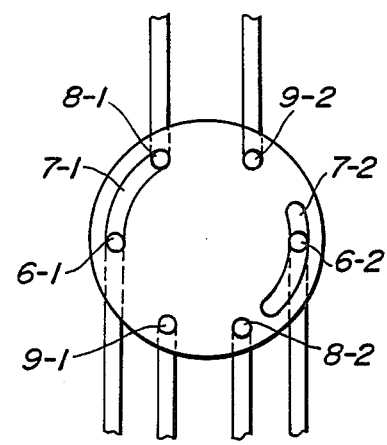
Figure 4C:
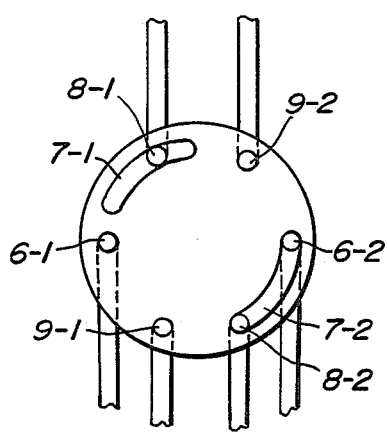

Then, by driving the motor 3-1, the detection plate 43 is rotated in a clockwise direction until the first suction sensor 46 detects the cut-out portion 44-1 in FIG. 2B. At this position, the state of the rotary valve 5A-1 has been changed into the first reagent sucking state such that the first common hole 6-1 and the first suction hole 8-1 are connected with each other through the long recess 7-1 as shown in FIG. 4B. In this state, the delivery syringe 1-1 is actuated when the two-way valves 24 and 22 are closed and the com-no passage is opened by turning the three-way valve 21 OFF, and the reagent is sucked from the first reagent tank 12-1 toward the flow-line 16-1 through the rotary valve 5A-1. After that, the state of the rotary valve 5A-1 is changed into the first reagent discharging state shown in FIG. 4E, and the sucked reagent is moved toward the delivery nozzle 14-1 by the discharging operation of the delivery syringe 1-1. The above operation is performed once or more until the flow-line from the first discharge hole 9-1 to a tip of the delivery nozzle 14-1 is filled with the washing liquid. In this case, it does not matter if a little amount of reagent remains in the flow-line from the first common hole 6-1 to the manifold block 15-1.

Figure 4D:
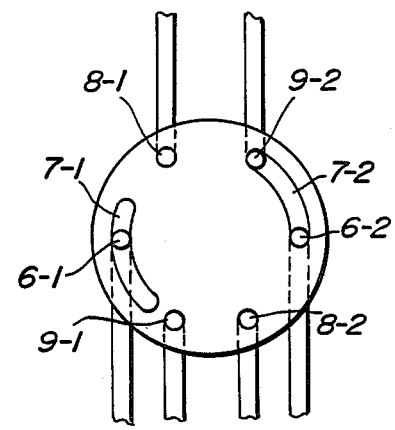
Figure 4E:
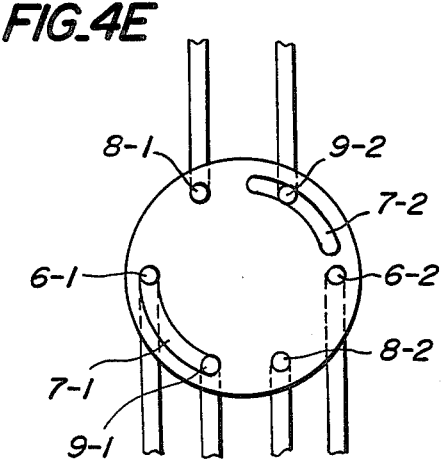

Then, by driving the motor 3-1, the detection plate 43 is rotated in an anti-clockwise direction until the second discharge sensor 48 detects the cut-out portion 44-1 in FIG. 2B, whereby the state of the rotary valve 5A-1 is changed into the second reagent discharging state such that the second common hole 6-2 and the second discharge hole 9-2 are connected with each other through the second long recess 7-2 as shown in FIG. 4D. In this state, as is the same as the explanation mentioned above, the operation for supplying the washing liquid is performed after the three-way valve 21 is turned ON, and the washing liquid is discharged from the delivery nozzle 14-2 through the com-nc passage of the three-way valve 21, the second common flow-lines 17-2 of the manifold blocks 15-2, 15-1, and the rotary valve 5A-1. In this manner, the flow-line from the delivery nozzle 14-2 to the rotary valve 5A-1 and all the flow-lines connected to the second long recess 7-2 and the second common hole 6-2 are filled with the washing liquid.

Then, by driving the motor 3-1, the detection plate 43 is rotated in a clockwise direction until the second suction sensor 47 detects the cut-out portion 44-2, thereby the state of the rotary valve 5A-1 is changed into the second reagent sucking state such that the second common hole 6-2 and the second suction hole 8-2 are connected with each other through the long recess 7-2 as shown in FIG. 4C. In this state, the delivery syringe 1-1 is actuated to effect the sucking operation under the condition that the two-way valves 24 and 22 are closed and the com-no passage is opened by turning the three-way valve 21 OFF, and the reagent is sucked from the second reagent tank 12-2 toward the flow-line 16-2 of the manifold block 15-1 through the rotary valve 5A-1. After that, the state of the rotary valve 5A-1 is changed into the second reagent discharging state shown in FIG. 4D, and the sucked reagent is moved toward the delivery nozzle 14-2 by the discharging operation of the delivery syringe 1-1. The above operation is performed once or more until the flow-line from the second discharge hole 9-2 to a tip of the delivery nozzle 14-2 is filled with the reagent.

Heretofore, the initializing operation of the rotary valve 5A-1 has been explained, but the initializing operations of the other rotary valves 5B-1, 5C-1 and 5D-1 can be simultaneously effected in the same manner as mentioned above since the rotary valves 5A-1 to 5D-1 exhibit the same state at the same time.

After the end of the initializing operation for the unit 2-1, respective rotary valves 5A-1 to 5D-1 of the unit 2-1 are returned to the home state, and the same initializing operation for the unit 2-2 is started.

(2) Delivery operation of reagent into reaction vessel:

After the end of all the initializing operations, the unit 2-1 and/or 2-2 are selected, and the reagents are simultaneously or separately delivered by the delivery syringes 1-1 to 1-4 through the units. Hereinafter, successive delivery operation for two kinds of reagents for one test item will be explained. At first, the state of the rotary valve 5A-1 is changed from the home state shown in FIG. 4A into the first reagent sucking state shown in FIG. 4B under the condition that the three-way valve 21 is OFF and the two-way valves 22 and 24 are closed. In this state, a predetermined amount of reagent is sucked from the first reagent tank 12-1 by the sucking operation of the deivery syringe 1-1. An amount of sucked reagent may be slightly larger than the predetermined amount, i.e. an amount to be delivered. As a result, the predetermined amount of reagent is sucked into the flow-line from the first common hole 6-1 to the flow-line 16-1 of the manifold block 15-1. Then, the state of the rotary valve 5A-1 is changed into the second reagent sucking state shown in FIG. 4C. In this state, a predetermined amount of reagent is sucked from the second reagent tank 12-2 by the sucking operation of the delivery syringe 1-1 into the flow-line from the second common hole 6-2 to the flow-line 16-2 of the manifold block 15-1.

After that, the state of the rotary valve 5A-1 is changed into the second reagent discharging state shown in FIG. 4D by rotating it in an anti-clockwise direction. In this state, the delivery syringe 1-1 is actuated under the condition that the three-way valve 21 is turned ON and the com-nc passage is opened, so that a predetermined amount of the second reagent is discharged from the delivery nozzle 14-2 into the reaction vessel 13 travelling just beneath the delivery nozzle 14-2. Further, the state of the rotary valve 5A-1 is changed into the first reagent discharging state shown in FIG. 4E by rotating it in an anti-clockwise direction. In this state, a predetermined amount of first reagent is discharged from the delivery nozzle 14-1 into the reaction vessel 13 travelling therebelow. Then, the three-way valve 21 is turned OFF, and the state of the rotary valve 5A-1 is returned to the home state shown in FIG. 4A by rotating it in a clockwise direction.

Then, the two-way valves 22, 24 are opened and the pump 29 is actuated, so that the washing liquid is discharged through the first common flow-lines 17-1 of the manifold blocks 15-2, 15-1 to effect the washing operation for these flow-lines. Therefore, since the first common flow-lines 17-1 of the manifold blocks 15-2, 15-1 which are used as the common suction flow-line of the four kinds of reagents are washed, the contamination between reagents is completely avoided. Moreover, it is not always necessary to effect this washing operation every time the reagent delivery is carried out.

FIGS. 5A to 5F are timing charts showing the operations of the delivery syringe 1-1, the rotary valve 5A-1, the three-way valve 21, the two-way valves 22, 24 and the pump 29 during successive reagent delivery operations mentioned above.

FIGS. 6A to 6F are schematic views showing several embodiments of the automatic chemical analyzer comprising the reagent delivery device according to the invention. In FIGS. 6A to 6C and 6E, respective embodiments can analyze twenty-four test items by one analyzing unit 71 having 24 channels as shown in FIG. 6A, two analyzing units 73-1, 73-2 each having 12 channels as shown in FIG. 6b, three analyzing units 75-1 to 75-3 each having 8 channels as shown in FIG. 6C or six analyzing units 79-1 to 79-6 each having 4 channels as shown in FIG. 6E. Moreover, in FIGS. 6D and 6F, respective embodiments can analyze thirty-two test-items by four analyzing units 77-1 to 77-4 each having 8 channels as shown in FIG. 6D or eight analyzing units 79-1 to 79-8 each having 4 channels as shown in FIG. 6F. In each embodiment, a plurality of racks 83 each supporting a plurality of sample cups 82 are set in a rack supply portion 81, and successive racks 83 are travel into a rack store portion 86 through a predetermined travelling passage 85 under the control of a controller 84. During this travelling of the rack 83, a sample contained in respective sample cups 82 is delivered into one or more reaction vessels arranged in a reaction line 87 of each analyzing unit in accordance with the number of test items, i.e. the number of channels in each analyzing unit to effect a predetermined analyzing operation.

Respective analyzing units comprise four delivery syringes. Therefore, in the analyzing unit 71 shown in FIG. 6A, use is made of six units 2-1 to 2-6 having the same construction as that mentioned above each including four rotary valves as shown in FIG. 7A, and respective delivery syringes 1-1 to 1-4 having two manifold blocks 91-1, 91-2 each having six flow-lines. Moreover, respective rotary valves of each unit are connected to relevant delivery syringes through the manifold block as is the same as the embodiment shown in FIG. 1. In this manner, six rotary valves i.e. twelve kinds of reagents, can be selectively delivered by one delivery syringe. Further, in the embodiment shown in FIG. 6B, each analyzing unit 73-1, 73-2 has three units 2-1 to 2-3 whose rotary valves are respectively connected to the delivery syringes 1-1 to 1-4 through the manifold blocks 91 each having six flowlines, as shown in FIG. 7B.

Figure 7C:
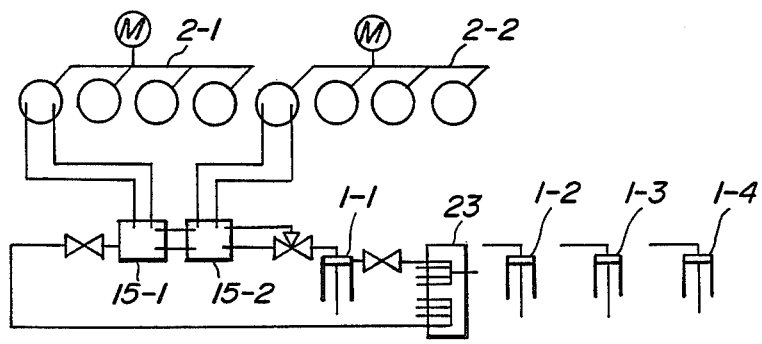
Figure 7D:
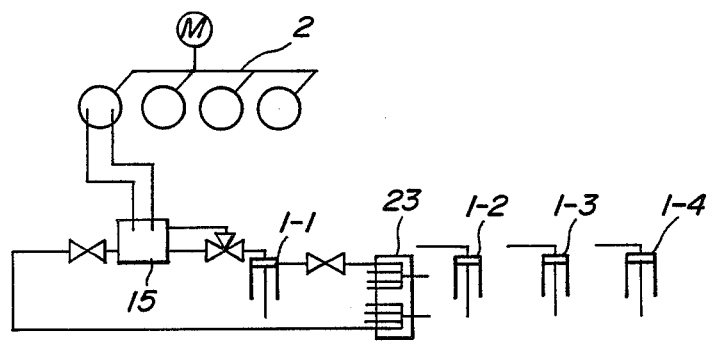

In the analyzing units each having eight channels shown in FIGS. 6C and 6D, use is made of two units 2-1 and 2-2 as shown in FIG. 7C. Moreover, in the analyzing units each having four channels shown in FIGS. 6E and 6F, four rotary valves of one unit 2 are respectively connected to the delivery syringes 1-1 to 1-4 through the manifold blocks 15 each having two flow-lines as shown in FIG. 7D.

Therefore, according to the invention, an automatic chemical analyzer having a various number of channels can be easily realized, if a plurality of units each having four rotary valves corresponding to the four delivery syringes are prepared and the necessary number of units are connected to the delivery syringes. In this manner, the requirements of a user can be achieved swiftly and easily, and the maintenance and repairing operations can be also achieved easily. Further, since respective units have the same construction with each other, the manufacturing cost of the apparatus can be reduced.

Figure 8:
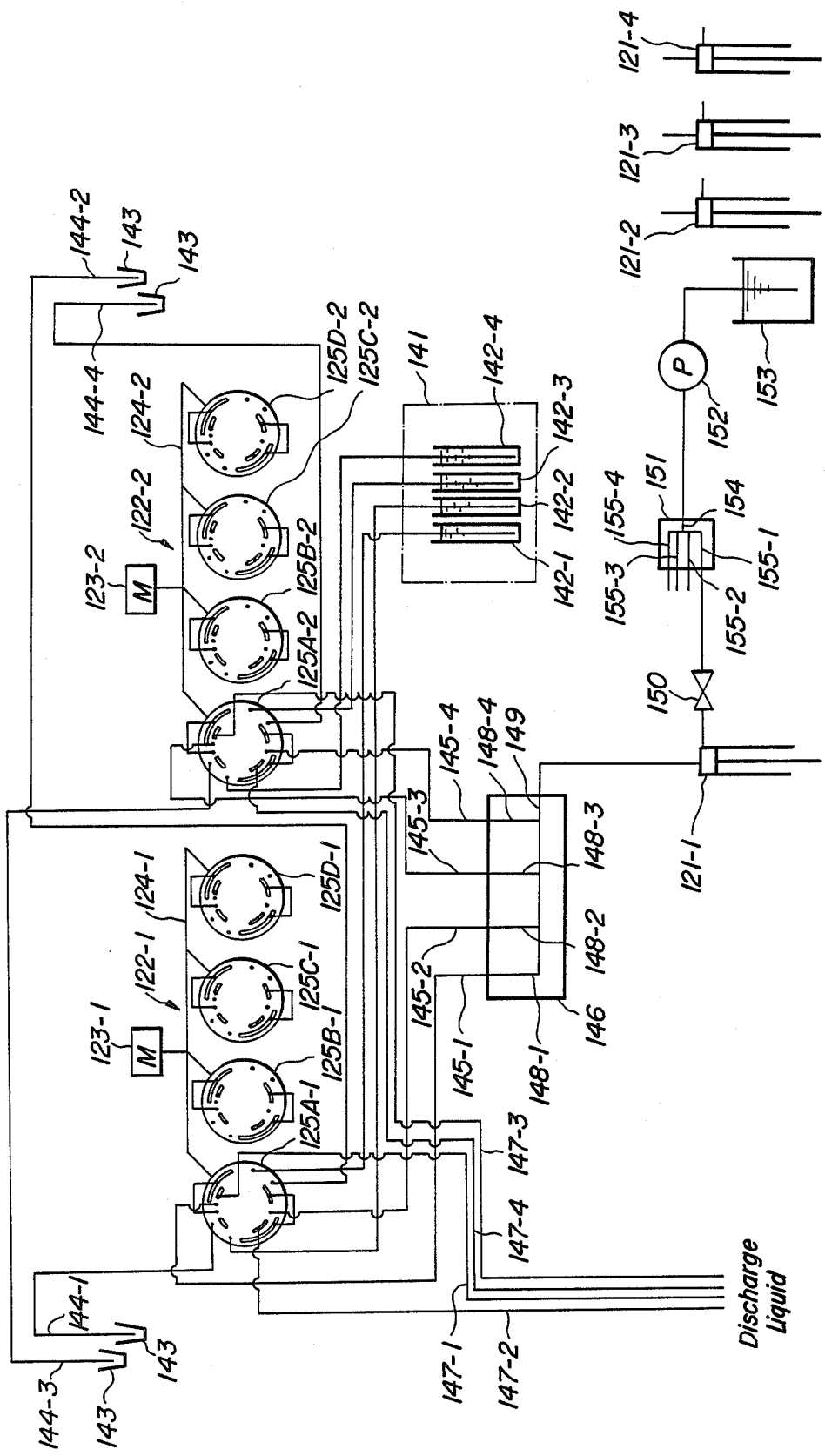
FIG. 8 is a schematic view depicting another embodiment of the reagent delivery device according to the invention.

FIG. 8 is a schematic view showing another embodiment of the reagent delivery device according to the invention, which can eliminate the contamination between reagents better than the embodiment shown in FIG. 1. In this embodiment, use is made of four delivery syringes 121-1 to 121-4 and two units 122-1 and 122-2.

Figure 9:
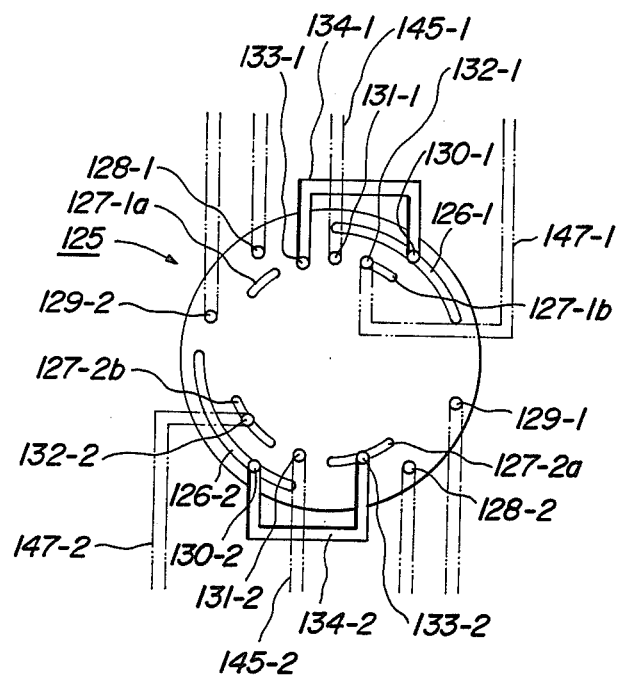
FIG. 9 is a schematic view showing one embodiment of the rotary valve used in the embodiment shown in FIG. 8.

The units 122-1 and 122-2 having the same construction comprise respectively motors 123-1 and 123-2 driven independently from each other and four rotary valves 125A-1 to 125D-1 and 125A-2 to 125D-2 which are simultaneously driven by these motors via driving mechanisms 124-1 and 124-2. Each rotary valve corresponds to one channel i.e. one test item, and functions to delivery selectively a first reagent and a second reagent. To this end, each rotary valve comprises two flow-line changing means. That is to say, as shown in FIG. 9 the rotary valve 125 comprises long recesses 126-1; 126-2 arranged along the same circumference and each constituting a first change-over valve of respective flow-line changing means, and long recesses 127-1a, 127-1b; 127-2a, 127-2b; arranged on the same smaller circumference and each constituting a second change-over valve of respective flow-line changing means. Furhter, the rotary valve 125 comprises discharge holes 128-1; 128-2 connected to the delivery syringe, suction holes 129-1; 129-2 connected to a reagent tank and connection holes 130-1; 130-2 connected to a first common flow-line which holes function to connect selectively the first common flow-line with the discharge holes 128-1; 128-2 and the suction holes 129-1; 129-2 via the long recesses 126-1; 126-2. Moreover, on the inner circumference are arranged common holes 1331-1; 131-2 connected to a second common flow-line which holes function to connect selectively the second common flow-line with the long recesses 127-1a, 127-1b; 127-2a, 127-2b, discharge holes 132-1; 132-2 connected to a waste liquid flow-line which function to connect selectively the waste liquid flow-line with the common holes 131-1; 131-2 via the long recesses 127-1b; 127-2b, and connection holes 133-1; 133-2 connected to the first common flow-line which function to connect selectively the first common flow-line with the common holes 131-1; 131-2 via the long recesses 127-1b; 127-2b. Further, the inner connection holes 133-1; 133-2 and the outer connection holes 130-1; 130-2 are respectively connected with each other through pipes 134-1; 134-2 to form the first common flow-line mentioned above.

In the unit 122-1, the suction holes 129-1 and 129-2 of one rotary valve 125A-1 are respectively connected to first and second reagent tanks 142-1 and 142-2 contained in a reagent refrigerator 141. The discharge holes 128-1 and 128-2 are respectively connected to delivery nozzles 144-1 and 144-2 arranged at predetermined positions through which a reaction vessel 143 containing a sample liquid to be tested is transported along a reaction line. Moreover, the common holes 131-1 and 131-2 are respectively connected to a manifold block 146 having four flow-lines through second common flow-lines 145-1 and 145-2. The discharge holes 132-1 and 132-2 are respectively connected to waste liquid flow-lines 147-1 and 147-2. The manifold block 146 comprises four flow-lines 148-1 to 148-4, and a common flow-line 149 connected to these flow-lines 148-1 to 148-4. The flow lines 148-1 and 148-2 are respectively connected to the common holes 131-1 and 131-2 through the second common flow-lines 145-1 and 145-2.

Also in the unit 122-2, the suction holes 129-1, 129-2 of the rotary valve 125A-2 are respectively connected to first and second reagent tanks 142-3, 142-4 contained in the reagent refrigerator 141. The discharge holes 128-1, 128-2 are respectively connected to delivery nozzles 144-3, 144-4 arranged at predetermined positions through which the reaction vessel 143 is transported along a reaction line. Moreover, the common holes 131-1, 131-2 are respectively connected to the flow-lines 148-3, 148-4 of the manifold block 146 through the second common flow-lines 145-3, 145-4, and the discharge holes 132-1, 132-2 are respectively connected to waste liquid flow-lines 147-3, 147-4.

The common flow-line 149, connected to the rotary valves 125A-1, 125A-2 respectively situated in the units 122-1, 122-2, is connected to the delivery syringe 121-1 to which a waste liquid tank 153 is connected through a valve 150, a branch block 151 and a pump 152. The branch block 151 comprises a main flow-line 154 and four branch flow-lines 155-1 to 155-4 connected to the main flow-line 154. Further, the main flow-line 154 is connected to the pump 152, and one branch flow-line 155-1 is connected to the valve 150.

Heretofore, the connection according to one delivery syringe 121-1 has been explained, but the other delivery syringes 121-2 to 121-4 have the same connection as explained above. For example, the delivery syringes 121-2, 121-3 and 121-4 are respectively connected to the rotary valves 125B-1, 125B-2; 125C-1, 125C-2 and 125D-1, 125D-2 through the manifold blocks each having four flow-lines. Further, respective delivery syringes 121-2 to 121-4 are connected to branch flow-lines of branch blocks through the respective valves.

In this manner, according to the embodiment mentioned above, a maximum of sixteen kinds of reagents can be selectively delivered by the delivery syringes 121-1 to 121-4. Further, if it is necessary to use further reagents, additional units may be connected to the delivery syringes 121-1 to 121-4 through manifold blocks each having additional flow-lines.

FIGS. 10A to 10C show another embodiment of the unit according to the invention. In this embodiment, use is made of four rotary valves, but only one rotary valve 125 is shown for the sake of simplicity. These four rotary valves are supported by a base 161, and respective drive shafts 162 of these rotary valves are connected through drive pins 165 to one end of valve drive shafts 164-1 to 164-4 rotatably secured to the base 161 via bearings 163. Respective drive pins 165 are supported by respective pin holders 166. To the valve drive shafts 164-1 to 164-4 are secured one end of respective levers 167-1 to 167-4, the other ends of which are connected to a connection plate 169 through bearings 168. In addition, the other end of one valve drive shaft (in FIGS. 10A to 10C the valve drive shaft 164-2) is connected to an output shaft 171 of the motor 123 through a coupling 170. In this manner, four valve drive shafts 164-1 to 164-4 i.e., respective drive shafts 162, are simultaneously driven through the levers 167-1 to 167-4 and the connection plate 169 by means of one motor 123. Further, coil springs 172 are respectively arranged between the levers 1567-1 to 167-4 and the pin holders 166.

The four rotary valves are constructed to be simultaneously driven between a home state, a second reagent sucking state, a first reagent sucking state, a washing state, a first reagent discharging state and a second reagent discharging state. In order to detect respective states mentioned above, a detection plate 173 is secured to the coupling 170 and two cut-out portions 174-1 and 174-2 are formed at predetermined positions in the detection plate 173. Then, the positions of the cut-out portions 174-1, 174-2 each representing the current states can be detected by means of a home sensor 175, a second suction sensor 176, a first suction sensor 177, a wash sensor 178, a first discharge sensor 179 and a second discharge sensor 180.

Hereinafter, the operation of this embodiment will be explained with reference to FIGS. 11A to 11F and FIGS. 12A to 12D.

Figure 11D:
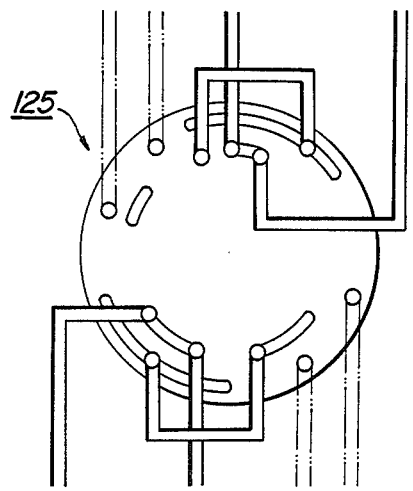
Figure 11E:
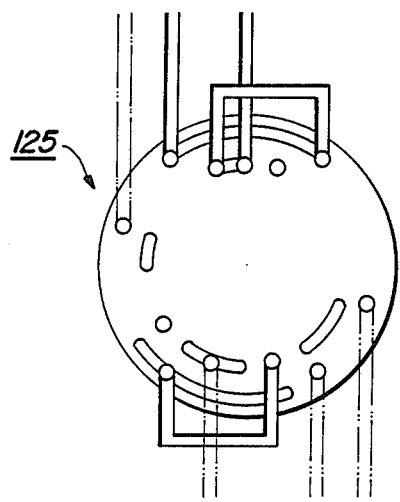

(1) Initialization of delivery device:

In this explanation, the operation of one rotary valve 125A-1 of the unit 122-1 will be explained, since the operations of the other rotary valves 125B-1 to 125D-1 and 125A-2 to 125D-2 are entirely the same as that of the valve 125A-1. At the home state in which the home sensor 175 detects the cutout portion 174-1 formed in the detection plate 173 (see FIG. 10B), the rotary valves of respective units maintain the state shown in FIG. 11A. At first, by driving the motor 123-1 of the unit 122-1, the detection plate 173 is rotated in an anti-clockwise direction until the first discharge sensor 179 detects the cut-out portion 174-2 in FIG. 10B. At this position, the home state has been changed into the first reagent discharging state such that the second common flow-line 145-1, the pipe 134-1 and the discharge hole 128-1 are connected with each other through the long recesses 126-1 and 127-1b as shown in FIG. 11E. In this state the pump 152 is actuated under the condition that the valve 150 is closed, and the washing liquid is discharged from the delivery nozzle 144-1 through the manifold block 146 and the rotary valve 125A-1.

Then, by driving the motor 123-1, the detection plate 173 is rotated in a clockwise direction until the first suction sensor 177 detects the cut-out portion 174-1 in FIG. 10B. At this position, the state of the rotary valve 125A-1 has been changed into the first reagent sucking state such that the second common flow-line 145-1, the pipe 134-1 and the suction hole 129-1 are connected with each other through the long recesses 126-1 and 127-1a as shown in FIG. 11C. In this state, the delivery syringe 121-1 is actuated, and the reagent is sucked from the first reagent tank 142-1 into the pipe 134-1 of the rotary valve 125A-1. After that, the state of the rotary valve 125A-1 is changed into the first reagent discharging state shown in FIG. 11E, and the sucked reagent is moved toward the delivery nozzle 144-1 by the discharging operation of the delivery syringe 121-1. The above operation is performed once or more until the flow-line from the discharge hole 128-1 to a tip of the delivery nozzle 144-1 is filled with the first reagent and the long recess 126-1, the pipe 134-1, and the long recesses 127-1a, 127-1b are filled with the washing liquid.

Figure 11F:
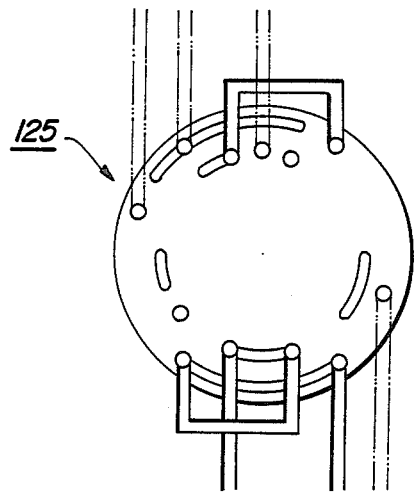

Then, by driving the motor 123-1, the detection plate 173 is rotated in an anti-clockwise direction until the second discharge sensor 180 detects the cut-out portion 174-2 in FIG. 10B, whereby the state of the rotary valve 125A-1 is changed into the second reagent discharging state such that the second common flow-line 145-2, the pipe 134-2 and the discharge hole 128-2 are connected with each other through the long recesses 126-2, 127-2b as shown in FIG. 11F. In this state, the operation for supplying the washing liquid is performed to discharge the washing liquid from the delivery nozzle 144-2.

Then, by rotating the motor 123-1, the detection plate 173 is rotated in a clockwise direction until the second suction sensor 147 detects the cut-out portion 174-1, whereby the state of the rotary valve 125A-1 is changed into the second reagent sucking state such that the second common flow-line 145-2, the pipe 134-2, and the suction hole 129-2 are connected with each other through the long recesses 126-2, 127-2a as shown in FIG. 11B. In this state, the delivery syringe 121-1 is actuated to effect the sucking operation under the condition that the valve 150 is closed, and the reagent is sucked from the second reagent tank 142-2 into the pipe 134-2 of the rotary valve 125A-1. After that, the state of the rotary valve 125A-1 is changed into the second reagent discharging state shown in FIG. 11F, and the sucked reagent is moved toward the delivery nozzle 144-2 by the discharging operation of the delivery syringe 121-1. The above operation is performed once or more until the flow-line from the discharge hole 128-2 to a tip of the delivery nozzle 144-2 is filled with the second reagent, and the long recess 126-2, the pipe 134-2, and the long recess 127-2b are filled with washing liquid.

Then, by driving the motor 123-1, the detection plate 173 is rotated in an anti-clockwise direction until the wash sensor 178 detects the cut-out portion 174-1 in FIG. 10B. At this position, the state of the rotary valve 125A-1 has been changed into the washing state such that the second common flow-line 145-1 and the waste liquid flow-line 147-1 are connected with each other through the long reces 127-1b and the second common flow-line 145-2 and the waste liquid flow-line 147-2 are connected with each other through the long recess 127-2b as shown in FIG. 11D. In this state, the pump 152 is actuated under the condition that the valve 150 is closed, and the washing liquid is discharged from the waste liquid flow-line 147-1; 147-2 through the manifold block 146 and the second common flow-lines 145-1; 145-2.

By effecting the operation mentioned above, the flow-line from a tip of the delivery nozzle 144-1 to the discharge hole 128-1 is filled with the first reagent. In addition, the flow-line from a tip of the delivery nozzle 144-2 to the discharge hole 128-2 is filled with the second reagent, and the other flow-lines are filled with the washing liquid.

Heretofore, the initializing operation of the rotary valve 125A-1 has been explained, but the initializing operations of the other rotary valves 125B-1, 125C-1 and 125D-1 can be simultaneously effected in the same manner as mentioned above since the rotary valves 125A-1 to 125D-1 exhibit the same state at the same time.

After the end of the initializing operation for the unit 122-1, respective rotary valves 125A-1 to 125D-1 of the unit 122-1 are returned to the home state, and the same initializing operation for the unit 122-2 is started.

(2) Delivery operation of reagent into reaction vessel:

After the end of all the initializing operations, the units 122-1 and/or 122-2 are selected, and the reagents are simultaneously or separately delivered by the delivery syringes 121-1 to 121-4 through the units. Hereinafter, successive delivery operations for two kinds of reagents will be explained. At first, the state of the rotary valve 125A-1 is changed from the home state shown in FIG. 11A into the second reagent sucking state shown in FIG. 11B by rotating the rotary valve 125A-1 by one step under the condition that the valve 150 is closed. In this state, a predetermined amount of reagent or a little more is sucked from the second reagent tank 142-1 by the sucking operation of the delivery syringe 121-1. As a result, the predetermined amount of reagent is sucked into the pipe 134-2 through the long recess 126-2. Then, the state of the rotary valve 125A-1 is changed into the first reagent sucking state shown in FIG. 11C. In this state, a predetermined amount of reagent or a little more is sucked from the first reagent tank 142-1 by the sucking operation of the delivery reagent 121-1 into the pipe 134-2 through the long recess 126-1.

After that, the state of the rotary valve 125A-1 is changed into the washing state shown in FIG. 11D by rotating the rotary valve 125A-1 by three steps. In this state, the pump 152 is actuated under the condition that the valve 150 is opened, and the washing liquid is flowed through the delivery syringe 121-1, the manifold block 146, the second common flow-lines 145-1; 145-2 and the long recesses 147-1; 147-2 to wash these flow-lines.

Then, the state of the rotary valve 125A-1 is changed into the first reagent discharging state shown in FIG. 11E by rotating the rotary valve 125A-1 by one step in an anti-clockwise direction. In this state, the delivery syringe 121-1 is actuated under the condition that the valve 150 is closed, thereby a predetermined amount of the first reagent is discharged from the delivery nozzle 144-1 into the reaction vessel 143 travelling just beneath the delivery nozzle 144-1. Further, the state of the rotary valve 125A-1 is changed into the second reagent discharging state shown in FIG. 11F by rotating it by one step in an anti-clockwise direction. In this state, a predetermined amount of a second reagent sucked by the delivery syringe 121-1 is discharged from the delivery nozzle 144-2 into the reaction vessel 143 travelling therebelow. Then, the state of the rotary valve 125A-1 is returned to the home state shown in FIG. 11A by rotating it in a clockwise direction.

FIGS. 12A to 12D are timing charts showing the operations of the delivery syringe 121-1, the rotary valve 125A-1, the valve 150 and the pump 152 during successive reagent delivery operations mentioned above.

According to the embodiment mentioned above, since the washing liquid is discharged from the waste liquid flow-lines 147-1; 147-2 through the delivery syringe 121-1, the manifold block 146 and the second common flow-lines 145-1; 145-2 to effect the washing operation, the contamination due to the diffusion of reagent into the second common flow-line can be effectively eliminated. In addition, if the reagent tank becomes empty, the second common flow-line is filled with the washing liquid and thus the delivery operation of the other reagents is not affected at all.

The present invention is not limited to the embodiments mentioned above, but various modifications are possible. For example, in case of the capacity of the delivery syringe being sufficiently larger than the necessary amount of the reagent to be delivered, the reagent sucking operations for the rotary valves by the delivery syringe connected to the unit are effected successively, and the sucked reagents are successively discharged. Moreover, the rotary valve can be constructed to treat one or more than two reagents, and the other sucking and discharging means such as a rotary pump can be used instead of the delivery syringe. Further, the number of rotary valves in one unit can be arbitrarily selected in accordance with the number of the sucking and discharging means. Furthermore, in the second embodiment, it is possible to wash the second common flow-line after the reagent discharging operation.

According to the invention, it is possible to delivery selectively a plurality of reagents without causing the contamination therebetween. In addition, even if the number of reagents to be delivered is increased, it is possible to deliver the reagents easily without increasing the number of sucking and discharging means.

What is claimed is:
1. A reagent delivery device comprising:
a plurality of sucking and discharging means;
a plurality of like-constructed units connected to said sucking and discharging means, each unit having valves the number of which corresponds to the number of said sucking and discharging means, and driving means for simultaneously driving said valves;
a plurality of reagent tanks connected to said valves in which a plurality of reagents are respectively contained;
a plurality of delivery nozzles connected to said valves; and
a plurality of like-constructed manifold block means connected to said sucking and discharging means and being readily attachable to and detachable from one another, said units and said sucking and discharging means, each said manifold block means having a plurality of flow lines for connecting a corresponding sucking and discharging means to one of said valves in each respective unit;
whereby respective delivery nozzles and reagent tanks are selectively connected to said sucking and discharging means by an operation of said valves; and
further whereby the number of reagents can be increased by simply providing additional delivery nozzles and likeconstructed units, connected to said sucking and discharging means through additional like-constructed manifold block means or manifold block means having additional flow lines, without additional sucking and discharging means.

2. A reagent delivery device according to claim 1, further comprising a washing means for flowing a washing liquid through said sucking and discharging means and said manifold block means.

3. A reagent delivery device according to claim 2, wherein the washing liquid is flows through said valves.

4. A reagent delivery device according to claim 1, wherein each of said valves is a rotary valve and each rotary valve has one or more flow-line changing means corresponding to the number of said reagents to be delivered by means of the relevant rotary valve, said flow-line changing means arranged in the same circumference.

5. A reagent delivery device according to claim 3, wherein each of said valves is a rotary valve and each rotary valve has one or more flow-line changing means corresponding to the number of said reagents to be delivered by means of the relevant rotary valve, each of said flow-line changing means comprising passages arranged concentrically on two circumferences and a conduit connecting inner and outer passages.

6. A reagent delivery device according to claim 1, wherein each said sucking and discharging means is a delivery syringe.

7. A reagent delivery device comprising:
four sucking and discharging means;
two like-constructed units connected to said sucking and discharging means;
four rotary valves in each of said units, each rotary valve having two flow-line changing means, each of said flow-line changing means comprising passages arranged concentrically on two circumferences and a conduit connecting inner and outer passages;

driving means for simultaneously driving said rotary valves;

two reagent tanks connected to each of said rotary valves, each said reagent tank containing a reagent;

two delivery nozzles connected to each of said rotary valves; and manifold block means connected to said sucking and discharging means, said manifold block means comprising four like-constructed manifold blocks which are readily attachable to and detachable from one another, said units and said sucking and discharging means, each manifold block including four branch flow-lines connected to a common flow-line, two of the branch flow-lines being further connected to a rotary valve in one of the respective units, the other two branch flowlines being further connected to a rotary valve in the other of the respective units, and the common flow-line being further connected to one of the sucking and discharging means;

whereby respective delivery nozzles and reagent tanks are selectively connected to said sucking and discharging means by an operation of said rotary valves; and further whereby the number of reagents can be increased by simply providing additional delivery nozzles and likeconstructed units, connected to said sucking and discharging means through additional like-constructed manifold blocks or manifold blocks having additional flow lines, without additional sucking and discharging means.

\* \* \* \* \*